(12) United States Patent
Miura et al.

(10) Patent No.: US 8,920,398 B2
(45) Date of Patent: Dec. 30, 2014

(54) ABSORBENT ARTICLE HAVING A PAIR OF REAR SIDE FLAPS

(75) Inventors: Tsunetoshi Miura, Kobe (JP); Yoko Munakata, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 1719 days.

(21) Appl. No.: 11/289,812

(22) Filed: Nov. 30, 2005

(65) Prior Publication Data

US 2006/0116652 A1   Jun. 1, 2006

Related U.S. Application Data

(60) Provisional application No. 60/631,759, filed on Nov. 30, 2004, provisional application No. 60/638,695, filed on Dec. 22, 2004.

(51) Int. Cl.
*A61F 13/536* (2006.01)
*A61F 13/47* (2006.01)
*A61F 13/15* (2006.01)
*A61F 13/472* (2006.01)

(52) U.S. Cl.
CPC ........... *A61F 13/47* (2013.01); *A61F 13/15203* (2013.01); *A61F 13/4702* (2013.01); *A61F 13/47236* (2013.01); *A61F 13/47245* (2013.01); *A61F 2013/15357* (2013.01); *A61F 2013/4706* (2013.01)
USPC ................ 604/385.31; 604/380; 604/385.101

(58) Field of Classification Search
CPC .............. A61F 13/476; A61F 13/4702; A61F 2013/4706; A61F 2013/15357
USPC .............................. 604/365–67, 378, 385.01, 604/385.03–385.04, 387, 385.31, 380, 604/385.101
See application file for complete search history.

(56) References Cited

U.S. PATENT DOCUMENTS 3,677,249 A * 7/1972 Kokx ............................. 604/366
4,045,833 A * 9/1977 Mesek et al. ...................... 5/484
(Continued)

FOREIGN PATENT DOCUMENTS

DE    29 703 589 U 1    7/1997
EP     1 016 393 A1    7/2000
(Continued)

OTHER PUBLICATIONS

Definition of "nonwovens", The Materials Handbook, pp. 565-566.*
(Continued)

*Primary Examiner* — Melanie Hand
*Assistant Examiner* — Paula L Craig
(74) *Attorney, Agent, or Firm* — George H. Leal; Amanda T. Barry; Andrew J. Hagerty

(57) ABSTRACT

An absorbent article having a pair of longitudinal edges, front and rear transverse edges, a front end region, a rear end region, and a central region disposed between the front and rear end regions. The ratio of the width of the rear end region to the width of the front end region ranges between 1:1 and 2.5:1. The absorbent article has a topsheet, backsheet, and an absorbent core disposed between the topsheet and the backsheet. The absorbent core has a pair of longitudinal edges and a pair of rear side flaps each extending laterally from the corresponding longitudinal edge of the absorbent core in the rear end region and a continuous support layer disposed on the backsheet in the rear end region. The continuous support layer includes a continuous material having a shear rigidity value of at least 3.0 gf/cm·degree in the longitudinal direction.

10 Claims, 5 Drawing Sheets

(56) References Cited

U.S. PATENT DOCUMENTS

| | | | |
|---|---|---|---|
| 4,059,114 A * | 11/1977 | Richards | 604/359 |
| 4,285,343 A * | 8/1981 | McNair | 604/387 |
| 4,392,862 A * | 7/1983 | Marsan et al. | 604/366 |
| 4,425,130 A | 1/1984 | DesMarais | |
| 4,589,876 A | 5/1986 | Van Tilburg | |
| 4,608,047 A * | 8/1986 | Mattingly | 604/387 |
| 4,687,478 A | 8/1987 | Van Tilburg | |
| 4,865,597 A * | 9/1989 | Mason et al. | 604/385.31 |
| 4,936,839 A * | 6/1990 | Molee et al. | 604/378 |
| 4,950,264 A | 8/1990 | Osborn, III | |
| RE33,351 E * | 9/1990 | Papajohn | 604/387 |
| 5,009,653 A | 4/1991 | Osborn, III | |
| 5,234,422 A | 8/1993 | Sneller et al. | |
| 5,267,992 A | 12/1993 | Van Tilburg | |
| 5,312,386 A | 5/1994 | Correa et al. | |
| 5,374,260 A | 12/1994 | Lemay et al. | |
| 5,389,094 A | 2/1995 | Lavash et al. | |
| 5,413,569 A * | 5/1995 | Yamamoto | 604/385.04 |
| 5,439,458 A | 8/1995 | Noel et al. | |
| 5,453,013 A | 9/1995 | Billings et al. | |
| 5,460,623 A | 10/1995 | Emenaker et al. | |
| 5,466,232 A | 11/1995 | Cadieux et al. | |
| 5,558,663 A | 9/1996 | Weinberger et al. | |
| 5,569,231 A | 10/1996 | Emenaker et al. | |
| H1698 H | 11/1997 | Lloyd et al. | |
| 5,704,931 A * | 1/1998 | Holtman et al. | 604/387 |
| 5,713,886 A * | 2/1998 | Sturino | 604/390 |
| 5,746,729 A | 5/1998 | Wada et al. | |
| 5,795,345 A | 8/1998 | Mizutani et al. | |
| 5,797,894 A | 8/1998 | Cadieux et al. | |
| 5,830,296 A | 11/1998 | Emenaker et al. | |
| 6,049,023 A | 4/2000 | Blenke et al. | |
| 6,074,376 A | 6/2000 | Mills | |
| 6,159,190 A * | 12/2000 | Tanaka et al. | 604/385.24 |
| 6,284,943 B1 * | 9/2001 | Osborn et al. | 604/366 |
| 6,300,538 B1 * | 10/2001 | Lindquist et al. | 604/369 |
| 6,326,525 B1 | 12/2001 | Hamajima et al. | |
| 6,503,233 B1 * | 1/2003 | Chen et al. | 604/385.01 |
| 6,506,961 B1 | 1/2003 | Levy | 604/380 |
| 6,515,195 B1 * | 2/2003 | Lariviere et al. | 604/380 |
| 6,517,525 B1 * | 2/2003 | Berthou et al. | 604/385.101 |
| 6,547,772 B1 * | 4/2003 | Suekane et al. | 604/385.04 |
| 6,563,013 B1 | 5/2003 | Murota | |
| 6,617,490 B1 * | 9/2003 | Chen et al. | 604/380 |
| 6,667,424 B1 | 12/2003 | Hamilton et al. | |
| 6,673,982 B1 * | 1/2004 | Chen et al. | 604/378 |
| 6,692,603 B1 | 2/2004 | Lindsay et al. | |
| 6,740,069 B2 | 5/2004 | Drevik | |
| 6,746,436 B1 * | 6/2004 | Sierri et al. | 604/385.04 |
| 6,986,761 B1 | 1/2006 | Hines et al. | |
| 7,056,311 B2 * | 6/2006 | Kinoshita et al. | 604/385.04 |
| 8,715,258 B2 * | 5/2014 | Munakata et al. | 604/385.101 |
| 2001/0009992 A1 * | 7/2001 | Boulanger et al. | 604/385.04 |
| 2001/0031956 A1 * | 10/2001 | Drevik | 604/385.04 |
| 2001/0039406 A1 * | 11/2001 | Hamajima et al. | 604/367 |
| 2002/0128622 A1 * | 9/2002 | Carvalho et al. | 604/385.01 |
| 2003/0023221 A1 * | 1/2003 | Kashiwagi et al. | 604/385.04 |
| 2003/0050617 A1 * | 3/2003 | Chen et al. | 604/378 |
| 2003/0055392 A1 * | 3/2003 | Tagami et al. | 604/378 |
| 2003/0088231 A1 * | 5/2003 | Yoshimasa et al. | 604/387 |
| 2003/0093054 A1 * | 5/2003 | Sierri et al. | 604/385.04 |
| 2003/0125700 A1 | 7/2003 | Drevik | |
| 2003/0153890 A1 * | 8/2003 | Rosenfeld | 604/385.04 |
| 2003/0187419 A1 * | 10/2003 | Bissah et al. | 604/385.01 |
| 2004/0068244 A1 * | 4/2004 | Salone et al. | 604/385.04 |
| 2004/0176734 A1 * | 9/2004 | Rasmussen et al. | 604/380 |
| 2004/0243087 A1 * | 12/2004 | Kinoshita et al. | 604/385.04 |
| 2004/0267224 A1 * | 12/2004 | Ulman | 604/385.04 |
| 2005/0137556 A1 * | 6/2005 | Brisebois | 604/385.04 |
| 2005/0148972 A1 * | 7/2005 | Miyama et al. | 604/380 |
| 2006/0116653 A1 | 6/2006 | Munakata et al. | |
| 2007/0055212 A1 * | 3/2007 | Kameo et al. | 604/385.04 |

FOREIGN PATENT DOCUMENTS

| | | |
|---|---|---|
| EP | 1208824 A2 * | 5/2002 |
| EP | 0858791 | 8/2002 |
| EP | 1 269 950 A | 1/2003 |
| JP | 2000-051269 | 2/2000 |
| JP | 2002-253612 | 9/2002 |
| JP | 2002-345888 | 12/2002 |
| JP | 2003-052743 | 5/2003 |
| WO | WO 95/15139 | 6/1995 |
| WO | WO 02/41817 A | 5/2002 |

OTHER PUBLICATIONS

"Dry-Laid Nonwoven Fabrics", Introduction to Textile Technology, p. 367.*
Translation of JP2003-052743.*
U.S. Appl. No. 11/289,844, filed Nov. 30, 2005, Yoko Munakata.
PCT International Search Report Dated Apr. 4, 2006.
Office Action for U.S. Appl. No. 11/289,844 dated Jun. 2, 2008; Munakata et al., filed Nov. 30, 2005.
Office Action for U.S. Appl. No. 11/289,844 dated Jun. 16, 2009; Munakata et al., filed Nov. 30, 2005.
Office Action for U.S. Appl. No. 11/289,844 dated Aug. 24, 2009; Munakata et al., filed Nov. 30, 2005.
Office Action, mailed Apr. 2, 2010, U.S. Appl. No. 11/289,844, filed Nov. 30, 2005, Inventors: Yoko Munakata, et al.

* cited by examiner

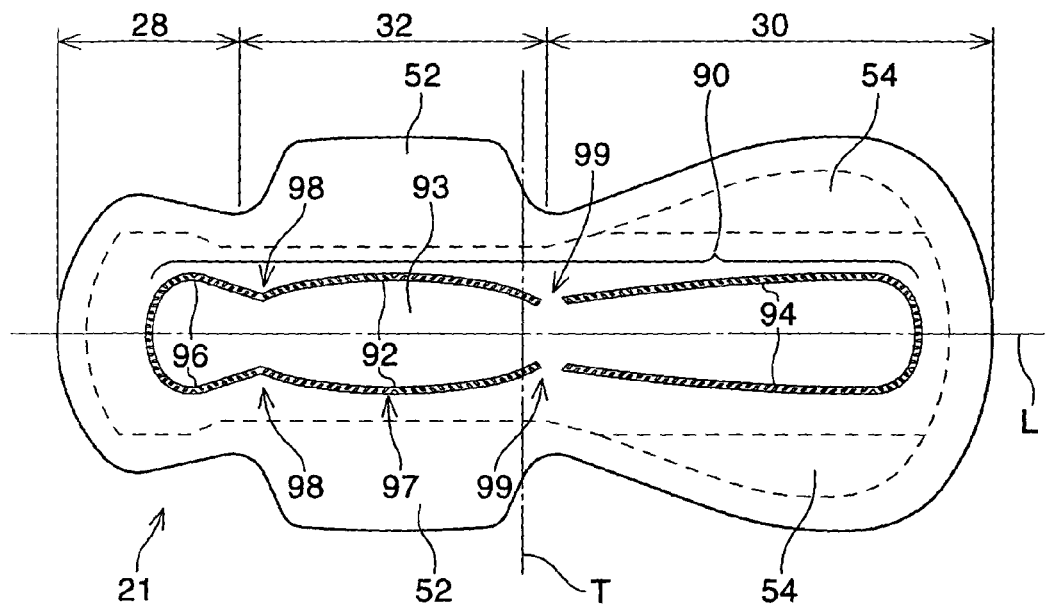
Fig. 8
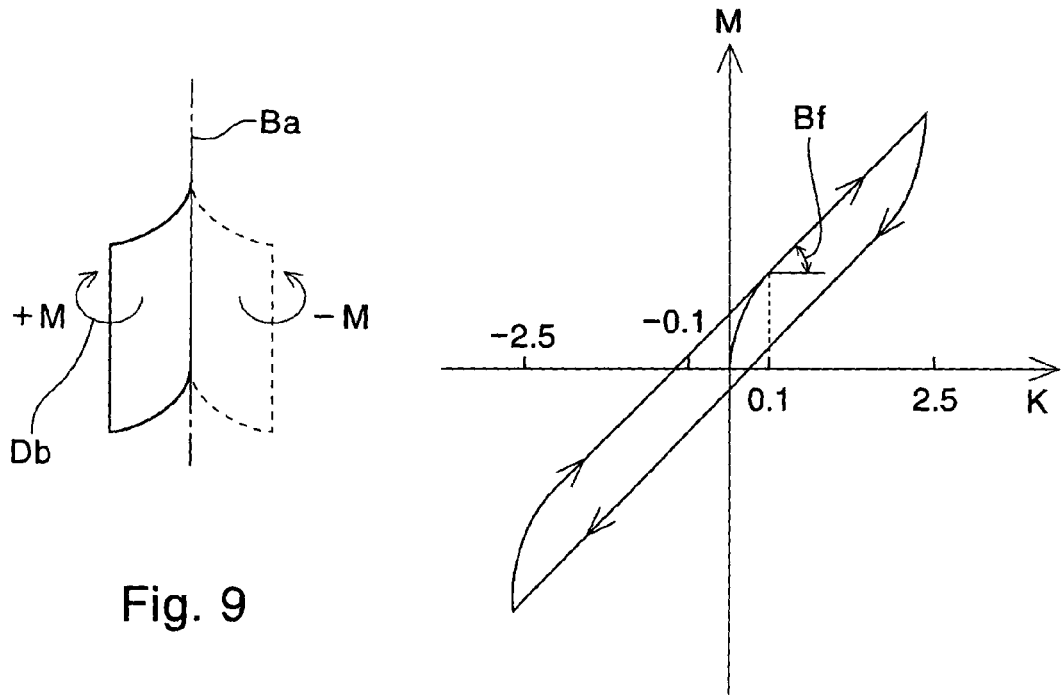
Fig. 9
Fig. 10

ABSORBENT ARTICLE HAVING A PAIR OF REAR SIDE FLAPS

CROSS REFERENCE TO RELATED APPLICATION

This application claims the benefit of U.S. Provisional Application Nos. 60/631,759 filed on Nov. 30, 2004 and 60/638,695 filed on Dec. 22, 2004.

FIELD OF THE INVENTION

The present invention relates to absorbent articles such as sanitary napkins, pantiliners, and incontinence pads. More particularly, the present invention relates to a sanitary napkin having a pair of rear side flaps.

BACKGROUND OF THE INVENTION

Absorbent articles, such as sanitary napkins, pantiliners, and incontinence pads, are typically worn in the crotch region of an undergarment. These devices are designed to absorb and retain liquids and other discharges from the human body to prevent body and garment soiling. The aforementioned types of absorbent articles are typically placed in a garment such as the wearer's panty and worn between the wearer's legs, adjacent to the genital (or fluids discharge source) area of the body.

Conventional relatively thick, overnight, or extra protection sanitary napkin products currently marketed in Japan provide protection from soiling by utilizing a combination of increased product length and thickness (which may include a profiled or varied caliper). These products, however, are not believed to conform or fit to the body of the wearer during the entire period of the products usage. Specifically, these products typically have a pair of rear side flaps in the rear end region which is placed or adhered (if desired) to the inside surface of undergarments in use. However, the rear side flaps tend to cause bunching (or tend to be deformed or twisted) by a stress or friction which is generated between the rear side flaps and the undergarment during use. This tends to not only affect the comfortness (i.e., the comfort feeling) of the wearer but also cause a situation that these products can not be positioned at the right place during the entire use thereby causing leakage of body fluids.

Thus, there is a need for an absorbent article that has rear side flaps which can be effectively prevented from bunching. There is another need for a sanitary napkin that can improve the comfortness of the wearer during the entire use of the napkin.

SUMMARY OF THE INVENTION

The invention is directed to an absorbent article having a pair of longitudinal edges, front and rear transverse edges, a front end region, a rear end region, and a central region disposed between the front and rear end regions. The front end region has a width defined between the longitudinal edges. The rear end region has a width defined between the longitudinal edges. The ratio of the width of the rear end region to the width of the front end region ranges between 1:1 and 2.5:1. The absorbent article comprises: a liquid pervious topsheet; a liquid impervious backsheet; an absorbent core disposed between the topsheet and the backsheet at least in the central region and the rear end region. The absorbent core has a pair of longitudinal edges. The absorbent article further comprises a pair of rear side flaps each extending laterally from the corresponding longitudinal edge of the absorbent core in the rear end region; and a continuous support layer disposed on the backsheet in the rear end region. The continuous support layer includes a continuous material which has a shear rigidity value of at least 3.0 gf/cm·degree in the longitudinal direction.

In another aspect of the invention, the absorbent article further comprises a uniform adhesive layer disposed between the continuous support layer and the backsheet in the rear end region, wherein the uniform adhesive layer uniformly bonds the continuous support layer to the backsheet in the rear end region.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

FIG. 8 is a top plane view of another preferred embodiment of the absorbent article of the present invention;

FIG. 9 is a schematic diagram of a specimen explaining the measurement for the bending stiffness;

FIG. 10 is a graph showing a hysteresis curve of a specimen;

DETAILED DESCRIPTION OF THE INVENTION

Herein, "comprise" and "include" mean that other elements and/or other steps which do not affect the end result can be added. Each of these terms encompasses the terms "consisting of" and "consisting essentially of".

Herein, "absorbent article" refers to articles which absorb and contain body exudates or discharges such as body fluids, and is intended to include sanitary napkins, pantiliners, diapers, and incontinence pads (and other articles worn in the crotch region of a garment).

Herein, "disposable" refers to articles which are intended to be discarded after a single use, composted, or otherwise disposed of in an environmentally compatible manner. (That is, they are not intended to be laundered or otherwise restored or reused as an absorbent article.)

Herein, "sanitary napkin" refers to articles which are worn by females adjacent to the pudendal region which are intended to absorb and contain the various exudates which are discharged from the body (e.g., blood, menses, and urine). It should be understood, however, that the present invention is also applicable to other feminine hygiene or catamenial pads such as pantiliners, diapers, and incontinence pads (and other articles worn in the crotch region of a garment).

Herein, "joined" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

Herein, "body surface" refers to surfaces of absorbent articles and/or their component members which face the body of the wearer, while "garment surface" refers to the opposite surfaces of the absorbent articles and/or their component members that face away from the wearer when the absorbent articles are worn. Absorbent articles and components thereof, including the topsheet, backsheet, absorbent core, and any individual layers of their components, have a body surface and a garment surface.

Figure 1:
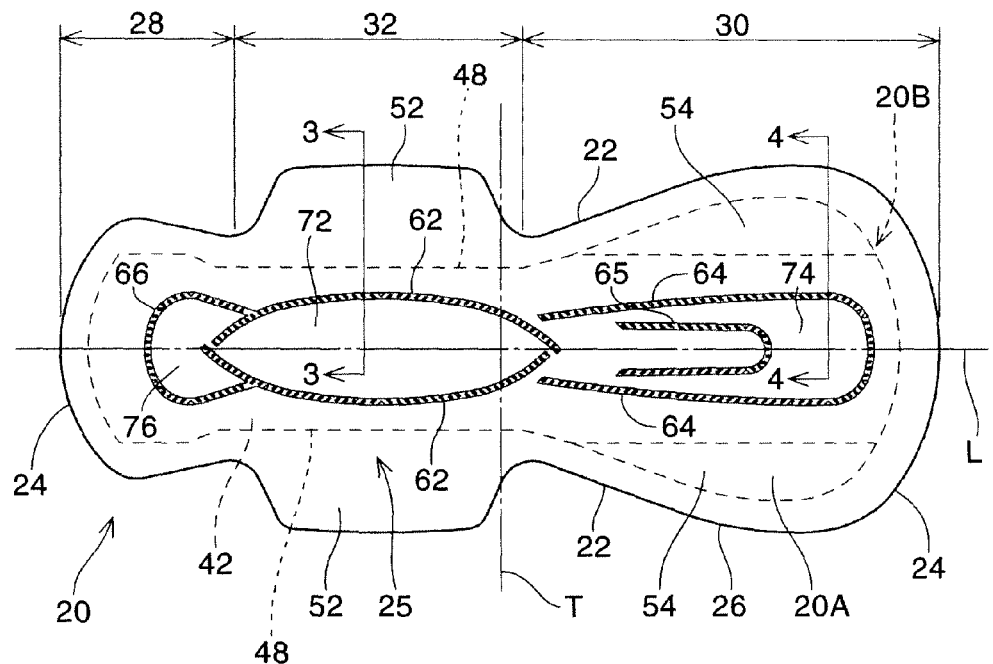
FIG. 1 is a top plane view of a preferred embodiment of the absorbent article of the present invention.

FIG. 1 is a top plane view of a preferred embodiment of the absorbent article of the present invention. In preferred embodiments shown in FIGS. 1-8, the absorbent article is a relatively thick, overnight, extra protection, disposable sanitary napkin 20.

Figure 2:
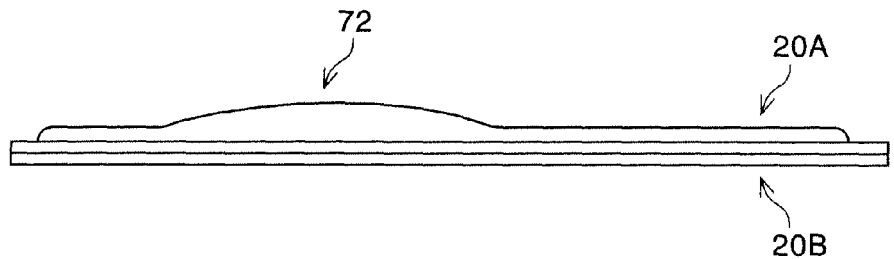
FIG. 2 is a side view of the absorbent article shown in FIG. 1.

The sanitary napkin 20 has two surfaces, a liquid pervious body-contacting surface or body surface 20A and a liquid impervious garment surface 20B. FIG. 2 is a side view of the sanitary napkin 20 shown in FIG. 1. The body surface 20A is intended to be worn adjacent to the body of the wearer. The garment surface 20B of the sanitary napkin 20 is on the opposite side and is intended to be placed adjacent to the wearer's undergarments when the sanitary napkin 20 is worn.

Referring to FIG. 1, the sanitary napkin 20 has two centerlines, a longitudinal centerline L and a transverse centerline T. Herein, "longitudinal" refers to a line, axis or direction in the plane of the sanitary napkin 20 that is generally aligned with (e.g., approximately parallel to) a vertical plane which bisects a standing wearer into left and right body halves when the sanitary napkin 20 is worn. Herein, "transverse" or "lateral" refers to a line, axis or direction which lies within the plane of the sanitary napkin 20 that is generally perpendicular to the longitudinal direction.

The sanitary napkin 20 has two spaced apart longitudinal edges 22 and two spaced apart transverse or end edges (or "ends") 24, which together form the periphery 26 of the sanitary napkin 20. The sanitary napkin 20 also has two end regions, i.e., a front end region 28 and a rear end region 30. A central region 32 is disposed between the end regions 28 and 30. The sanitary napkin 20 includes at least a pair of rear side flaps 54 in the rear end region 30. Preferably, the sanitary napkin 20 further includes a pair of central side flaps 52 in the central region 32. (In the preferred embodiments shown in FIGS. 1 and 8, the sanitary napkins 20 and 21 include both central side flaps 52 and rear side flaps 54.) Each pair of central and rear side flaps 52 and 54 extends laterally outward from a main body portion 25 in the central region 32 and the rear end region 30, respectively.

The front end region 28 is defined as the area that is placed to the front of the wearer's body when the sanitary napkin 20 is worn. The rear end region 30 is defined as the area that is placed to the rear of the wearer's body. The central region 32 is defined as the area that is generally located directly below the perineum of the wearer and which receives the greatest amount of menses.

In a preferred embodiment, each region can be defined with respect to the positions of the side flaps 52 and 54. The front end region 28 ends at the transition area where the traversal distance between the two longitudinal edges 22 starts to increase towards the central region 32 as shown in FIG. 1. Similarly, the rear end region 30 ends at the transition area where the traversal distance between the two longitudinal edges 22 starts to increase towards the central region 32 as shown in FIG. 1.

In other words, each region can be defied with respect to the curve of the longitudinal edge 22. The front end region 28 ends at the transition area where the curve of the longitudinal edge 22 starts to extend laterally outward at a higher rate than before as shown in FIG. 1. Similarly, the rear end region 30 ends at the transition area where the curve of the longitudinal edge 22 starts to extend laterally outward at a higher rate than before as shown in FIG. 1.

Figure 3:
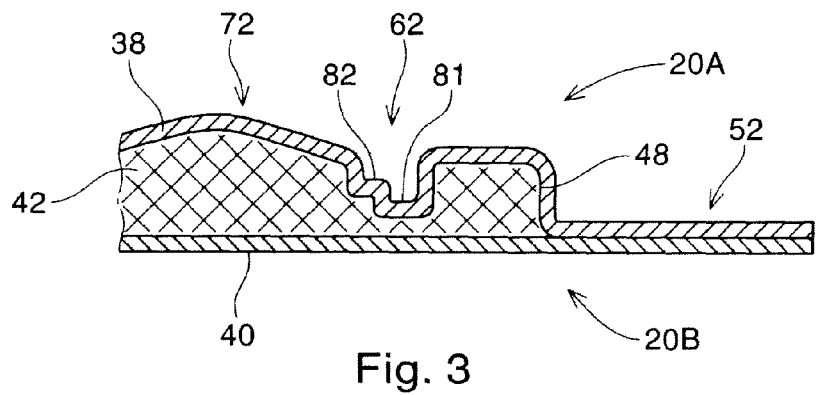
FIG. 3 is a schematic cross-sectional view of the absorbent article shown in FIG. 1 taken along line 3-3 of FIG. 1.

FIG. 3 is a cross-sectional view of the sanitary napkin 20 taken along the section line 3-3 in FIG. 1, which shows the individual components of the sanitary napkin 20 shown in FIG. 1. The sanitary napkin 20 shown in FIG. 3 generally comprises at least three primary components, i.e., a liquid pervious topsheet 38; a liquid impervious backsheet 40; an absorbent core 42 having longitudinal edges 48 disposed between the topsheet 38 and the backsheet 40. The central side flaps 52 extend laterally outward from the corresponding longitudinal edge 48 of the absorbent core 42 in the central region 32. The topsheet 38, backsheet 40, and absorbent core 42 can comprise any types of materials known in the art as being suitable for such components of an absorbent article or a sanitary napkin.

The topsheet 38 is preferably compliant, soft feeling, and non-irritating to the wearer's skin. Further, the topsheet 38 is liquid permeable or pervious, permitting body fluids (e.g., menses and/or urine) to readily penetrate through its thickness. A suitable liquid permeable material for the topsheet 38 may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet 38 includes a nonwoven web, the web may be manufactured by a wide number of known techniques. For example, the web may be spunbonded, carded, wet-laid, melt-blown, hydroentangled, combinations of the above, or the like.

A particularly suitable material for the topsheet 38 includes an apertured formed film. Apertured formed films are preferred for the topsheet 38 because they are pervious to body fluids and, if properly apertured, have a reduced tendency to allow liquids to pass back through and rewet the wearer's skin. Thus, the body surface of the formed film (i.e., the body surface 22A of the sanitary napkin 20) remains dry, thereby reducing body soiling and creating a more comfortable feel for the wearer. A preferred material for the topsheet 38 is a macroscopically expanded, three-dimensional formed polyethylene film. One preferred material for the topsheet 38 is available from Tredegar Film Products, Indiana, USA, under Code No. X-27121.

The backsheet 40 is impervious to body fluids and is preferably manufactured from a thin plastic film, although other flexible liquid impervious materials may also be used. Herein, "flexible" refers to materials which are compliant and will readily conform to the general shape and contours of the human body. The backsheet 40 prevents the body fluids absorbed and contained in the absorbent core 42 from wetting articles which contact the absorbent article such as bed sheets, pants, pajamas and undergarments. The backsheet 40 may thus include a woven or nonwoven material, polymeric films such as thermoplastic films of polyethylene or polypropylene, or composite materials such as a film-coated nonwoven material. The backsheet 40 can include a single layer material, or two or more layers of materials. The backsheet 40 preferably has a thickness of from about 0.012 mm (0.5 mil) to about 0.081 mm (3.4 mils). In a preferred embodiment, the backsheet 40 is a single layer polyethylene film. Such a preferred polyethylene film is available from Daedong Co. Ltd., KyungBuk-Do, Korea, under Code No. DNF-040712VL.

The backsheet 40 preferably has a microporous structure which can permit vapors to escape from the absorbent core 42 (often called "breathable backsheet") while still preventing body fluids from passing through the backsheet 40. A preferred microporous polyethylene film is available from Mitsubishi Chemical Corporation, Tokyo, Japan, under Code No. NPP2. The backsheet 40 can be embossed to provide a cloth-like appearance.

The absorbent core 42 is capable of receiving, absorbing or retaining body fluids discharged. The absorbent core 42 is preferably compressible, conformable, and non-irritating to the wearer's skin. The absorbent core 42 can be formed by a single layer material or a plurality layers of materials. The absorbent core may include any of a wide variety of liquid-absorbent materials commonly used in absorbent articles, such as comminuted wood pulp, which is generally referred to as airfelt. A particularly preferred absorbent core material is an airfelt material which is available from Weyerhaeuser Company, Washington, USA, under Code No. NB416.

Examples of other suitable absorbent materials for use in the absorbent core include creped cellulose wadding; melt-blown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; absorbent gelling materials; or any equivalent material or combinations of materials, or mixtures of these.

The absorbent core 42 may be manufactured in a wide variety of sizes and shapes. The periphery of the absorbent core 42 thus can take any shape in its top plane view. Preferred shapes for the core periphery include an oval, a rectangle, an hourglass, and a combination of the oval and rectangle such as the one shown in FIG. 1.

In a preferred embodiment for a relatively thick, overnight, extra protection sanitary napkin, the sanitary napkin 20 has a total core length ranging between about 200 and 450 mm. A length shorter than about 200 mm typically does not extend far enough into the gluteal area to provide improved protection. A length longer than about 400 mm generally extends too far beyond the gluteal groove in the rear end region to conform to the wearer's buttocks, causing a poor gluteal fit.

Figure 4:
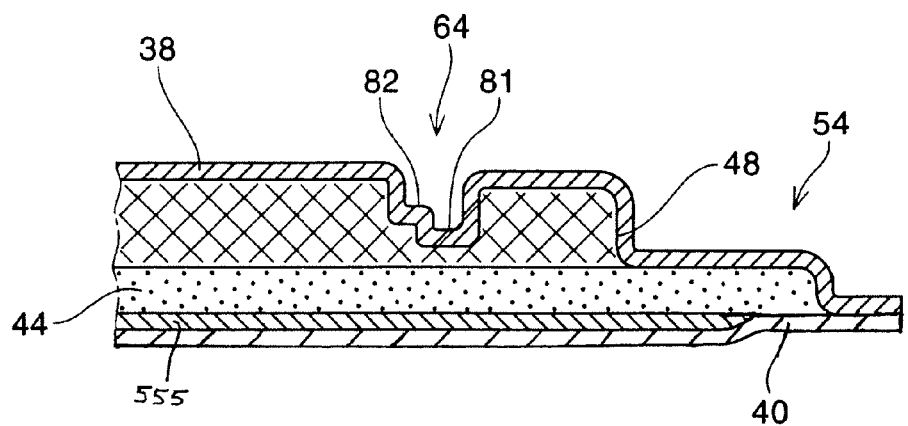
FIG. 4 is a schematic cross-sectional view of the absorbent article shown in FIG. 1 taken along line 4-4 of FIG. 1.

FIG. 4 is a schematic cross-sectional view of the sanitary napkin 20 shown in FIG. 1 taken along line 4-4 of FIG. 1. The rear side flaps 54 extend laterally outward from the corresponding longitudinal edge 48 of the absorbent core 42 in the rear end region 30. The sanitary napkin 20 further includes a continuous support layer 44 which is disposed between the topsheet 38 and the backsheet 40 in (at least a part of) the rear end region 30 (and the front region 28 and the central region 32 if desired). In the preferred embodiments shown in FIGs, the continuous support layer 44 is disposed between the absorbent core 42 and the backsheet 40. The continuous support layer 44 extends laterally into the rear side flaps 54 in the rear end region 30. Herein, "continuous layer" means a layer (or member) that does not include two (or more) component materials physically separated (or spaced apart) within the layer. For example, if a layer (or member) includes two component materials which are not directly bonded or connected one another, that layer is not a continuous layer but a discontinuous layer. The continuous support layer 44 should have sufficient thickness, rigidity and resiliency to prevent the rear side flaps 54 from bunching (i.e., deforming or twisting) which tends to be cased by a stress generated between the rear side flaps 54 and the undergarment during use.

Specifically, to effectively prevent the rear side flaps 54 from bunching, the continuous support layer preferably includes a continuous material which has a shear rigidity value of at least 3.0 gf/cm·degree, more preferably 4.0-10.0 gf/cm·degree, and yet more preferably 5.0-9.0 gf/cm·degree in the longitudinal direction. Herein, "in the longitudinal direction" means that the continuous material is sheared in the direction which is parallel to the longitudinal centerline L. By limiting the shear rigidity value within the above ranges, the rear side flaps 54 can be effectively prevented from bunching. For example, if the shear rigidity value is too low (e.g., lower than 3.0 gf/cm·degree), the rear side flaps 54 tends to easily cause bunching since in that event the rear side flaps 54 become too soft and are easily affected by the shear force (i.e., stress or friction) which is applied from the undergarment due to the wearer's movement. On the other hand, if the shear rigidity value is too high (e.g., higher than 10.0 gf/cm·degree), the rear side flaps 54 tend to affect the comfortness to the wearer since in that event the rear side flaps 54 become too stiff, and as a result, the wearer feels uncomfortable in use.

In addition, the continuous support layer preferably includes a continuous material which has a bending stiffness value of 0.4-10.0 gf·cm$^2$/cm, more preferably 0.5-7.0 gf·cm$^2$/cm, and yet more preferably 0.7-2.0 gf·cm$^2$/cm in the longitudinal direction. Herein, "in the longitudinal direction" means that the continuous material is bent with a bending axis which is parallel to the traversal centerline T. It should be noted that the bending stiffness value in the traversal direction can take any number, however, it is preferably within the same or similar range as that for the longitudinal direction. By limiting the bending stiffness value within the above ranges, both comfortness and easy handling of the absorbent article can be achieved. For example, if the bending stiffness value is too low (e.g., lower than 0.4 gf·cm$^2$/cm), the rear side flaps 54 tend to be too soft and flexible, and as a result, they are easily folded when the absorbent article is applied to the undergarment by the wearer. On the other hand, if the bending stiffness value is too high (e.g., higher than 10.0 gf·cm$^2$/cm), the rear side flaps 54 tend to affect the comfortness to the wearer since in that event the rear side flaps 54 do not fully conform to the curve of the body, and as a result, the wearer feels uncomfortable in use.

The continuous support layer 44 can be formed by a wide variety of materials (preferably hydrophilic), preferably fibrous materials. Preferred fibrous materials include nonwoven materials. The fibers or other components of such nonwoven materials may be synthetic or natural, or partially synthetic and partially natural. Suitable synthetic fibers include polyester, polypropylene, polyethylene, nylon, viscous rayon, or cellulose acetate fibers. Suitable natural fibers include cotton, cellulose, or other natural fibers. In preferred embodiments, the continuous support layer 44 includes a nonwoven material which has a basis weight of 40-200 g/m$^2$, preferably 60-100 g/m$^2$.

In one preferred embodiment, the continuous support layer 44 is an air laid nonwoven material. A preferred material is available from Kang Na Hsiung Enterprise Co., Ltd., Taipei, Taiwan, under Code No. AL080-BL01-10. This nonwoven material has basis weight of 80 g/m$^2$, density of 0.07 g/cm$^3$, and thickness of 1.16 mm. This nonwoven material is formed by a mixture of chemical pulp (or cellulose) fibers and polyethylene/polypropylene bi-component fibers through an air through process. In order to provide the desired support effect for the rear side flaps 54 under in-use conditions, it is desirable that the nonwoven material for the continuous support layer 44 preferably has basis weight of 30~180 g/m$^2$, density of 0.05~0.20 g/cm$^3$, and thickness of 0.3~1.5 mm.

Referring again to FIG. 4, the sanitary napkin 20 preferably includes an adhesive layer 555 disposed between the continuous support layer 44 and the backsheet 40 in the rear end region 30. Preferably, the adhesive layer is applied uniformly (thereby forming a uniform adhesive layer) between the continuous support layer 44 and the backsheet 40. Herein, "uniform layer" refers to a layer that has a basis weight with a deviation of no more than 20% at every unit area within the layer. Herein, "unit area" is defined as an area of 12.5mm× 50mm Thus, in this embodiment the uniform adhesive layer preferably contains an adhesive which has a basis weight with a deviation of no more than 20% at every unit area within the layer. As a result, the uniform adhesive layer can uniformly bond the continuous support layer 44 to the backsheet 40 in the rear end region 30. Preferably, the uniform adhesive layer is formed by a hot-melt adhesive. In preferred embodiments, the uniform adhesive layer has a basis weight of about 1.0-13 g/m$^2$, more preferably 2.0-10g/m$^2$. In a preferred embodiment, the uniform adhesive layer has a basis weight of about 3.6 g/m$^2$. Such a uniform adhesive layer is preferred since it can help provide a uniform thickness, rigidity and/or resiliency to the rear side flaps 54 which can also prevent the rear side flaps 54 from bunching which may be cased by a stress generated between the rear side flaps 54 and the undergarment during use.

The topsheet 38, the backsheet 40, the absorbent core 42 may be assembled in a variety of configurations known in the art. Preferred configurations are described in U.S. Pat. Nos. 4,950,264; 5,009,653 issued to Osborn; U.S. Pat. No. 4,425, 130 issued to DesMarais; U.S. Pat. Nos. 4,589,876 and 4,687, 478 issued to Van Tilburg, and U.S. Pat. No. 5,234,422 issued to Sneller, et al.

Referring again to FIG. 1, the sanitary napkin 20 has a pair of outwardly convex longitudinal central channels 62 formed at least in the central region 32. Herein, "channel" refers to a generally elongated depression formed in at least a portion of an absorbent article. The channel can be formed by, for example, reducing the amount of the absorbent core at the channel portion, and/or compressing or embossing the absorbent core at the channel portion.

Typically, the channel is formed by applying a compressive force to both the topsheet and the absorbent core toward the backsheet. The topsheet at the channel portion is pushed down into the absorbent core, and the materials of the topsheet and the absorbent core are compressed at and below the bottom of the channel portion. By this operation (which is often called "embossing process"), the channel portion of the absorbent article has relatively higher density than the other portion(s) or the surrounding portion(s) of the channel portion. The channels of the present invention can be formed by any structures and processes known in the art.

The channel tends to preferentially diffuse or lead body fluids flow along the direction in which the channel extends. Therefore, the channel is useful to control body fluids flow within the absorbent article thereby preventing body fluids leakage from the absorbent article. The channel also tends to work as a preferential bending axis of the absorbent article. Therefore, the absorbent article may bend at the channel portion such that it provides an improved fit of the absorbent article to the wearer's body. It should be noted that such an improved fit of the absorbent article can also contributes an improvement in preventing body fluids leakage from the absorbent article.

The channel of the present invention can be either continuous or discontinuous. Herein, "discontinuous" means the channel can be separated by a non-channel portion (i.e., a portion where no channel is formed) such that the channel includes 2 or more elongated channel portions which are separated by a non-channel portion. The distance between the two succeeding channel portions (i.e., the length of the no channel portion) may be changed depending on the product design. Preferably, the length of the no channel portion is 0-20 mm, more preferably 2-10 mm, and yet more preferably 3-6 mm.

In one preferred embodiment, channels are formed by applying a uniform (or a single level of) compressive force to the topsheet and the absorbent core toward the backsheet. Alternatively, channels can be formed by applying two or more levels of compressive forces to the topsheet and the absorbent core toward the backsheet thereby forming a "two (or more) stage channel structure".

In the preferred embodiment shown in FIG. 1, the channels 62, 64, 65 and 66 are formed by applying two levels of compressive forces to the topsheet 38 and the absorbent core 42 toward the backsheet 40. The application of the two levels of compressive forces (i.e., higher compression and lower compression) produces two stage depth portions (i.e., "two stage channel structure") in the resulting the channels, i.e., first portion and second portion.

Figure 5:
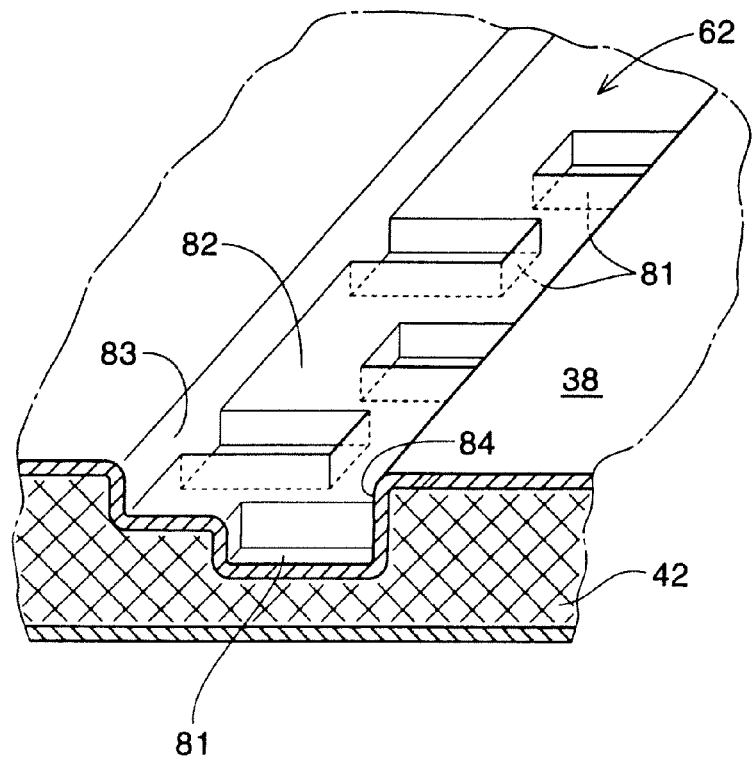
FIG. 5 is a perspective view of an emboss channel formed in the absorbent article shown in FIG. 1.

FIG. 5 is a perspective view of one channel formed in the sanitary napkin 20 shown in FIG. 1. In this embodiment, the channel 62 has two side walls (or channel walls) 83 and 84. The first portions 81 are formed by a higher compression, while the second portion 82 is formed by a lower compression. The absorbent core 42 is more compressed at the portions 81 of higher compression than the portion 82 of lower compression. In the embodiment shown in FIG. 5 (and also FIG. 3), the portions 81 of higher compression form the lowest portions of the channel 62, while the portion 82 of lower compression forms the higher portion in the channel 62. The first portions 81 of higher compression have a higher density than the portion 82 of lower compression as a result of compression force differences. Such a two stage channel structure is preferred since it can provide a better comfort to the wearer's body in use compared with the channel structure which has no stage difference (formed by no compression force differences applied). In addition, since the compression force is more concentrated at the portions 81 of higher compression, the two stage channel structure can also increase the bonding strength between the topsheet 38 and the absorbent core 42 at the portions 81.

The first portions 81 formed by a higher compression extend from one channel wall 83 but does not reach the other channel wall 84. In the embodiment shown in FIG. 5, the shape of the first portions 81 formed by a higher compression is about a rectangular. However, the shape of the first portions

81 can vary depending on the channel design in the sanitary napkin 20. The length, width and depth of the first portions 81 can also vary depending on the channel design in the sanitary napkin 20. Similarly, the shape, the length, width and depth of the second portion 82 can also vary depending on the channel design in the sanitary napkin 20.

The first portions 81 formed by a higher compression are spaced one another. The distance or interval of two adjacent portions 81 can be either consistent or inconsistent. In the embodiment shown in FIG. 5, the distance of two adjacent portions 81 is consistent.

In an alternative embodiment (not shown in FIGs.), the first portions 81 may be formed by lower compression, and the second portion 82 may be formed by higher compression. This produces an opposite geographic shape of the channels.

A variety of preferred channel structures which are applicable to the present invention are disclosed in, for example, U.S. Pat. No. 6,563,013 issued to Murota on May 13, 2003. This publication discloses examples of "two stage channel structure" which are preferably applicable to the embodiments of the present invention.

In the embodiment shown in FIG. 5, the first portion 81 formed by a higher compression extends from one channel wall 83 but does not reach the other channel wall 84. This channel structure is referred to as a "stitched channel structure".

However, this is not always necessary. Alternatively to such a stitched channel structure, the first portion 81 formed by a higher compression can extend from one channel wall 83 to the other channel wall 84. Such a structure can be produced by an application of higher and lower compressions alternatively applied along the longitudinal direction of the channel 62. Such channel structures are disclosed in, for example, U.S. Pat. No. 5,795,345 issued to Mizutani et al. on Aug. 18, 1998.

Figure 6:
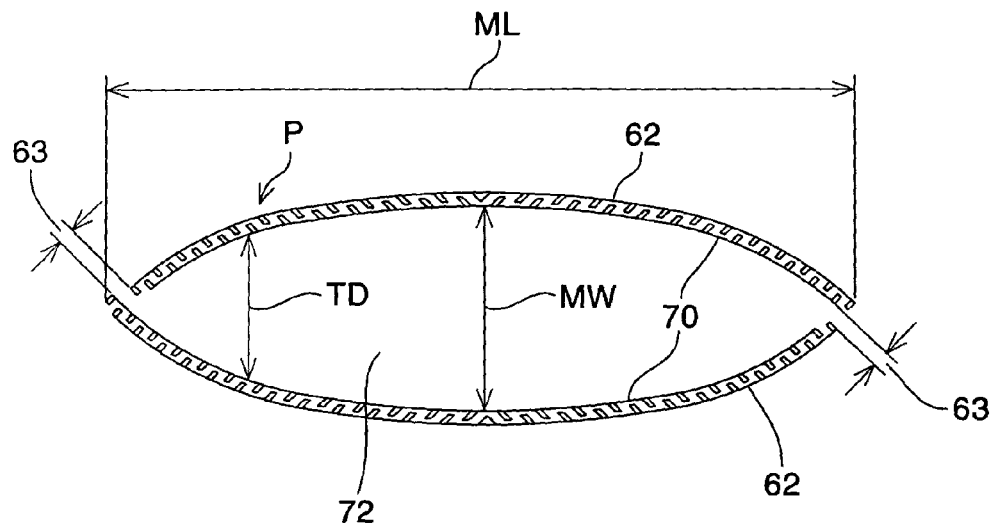
FIG. 6 is a plane view of the pair of outwardly convex longitudinal channels shown in FIG. 1.

FIG. 6 is a plane view of the pair of outwardly convex longitudinal central channels 62 shown in FIG. 1. Herein, "outwardly convex" means the longitudinal channels have a curved line shape (including a polygonal lines shape and a curved line shape) which is outwardly extended when looking from the longitudinal centerline L. The longitudinal central channels 62 shown in FIG. 1 have a circular arc shape which is outwardly curved when looking from the longitudinal centerline L of the sanitary napkin 20. The traversal distance TD of the pair of outwardly convex longitudinal central channels 62 decreases towards the both ends of the central channels 62 to define a central closed area 72.

Herein, "closed area" is an area that is disposed between the inside channel wall(s) of the outwardly convex longitudinal channels. When the traversal distance between the inside channel walls of the outwardly convex longitudinal channels reaches 60% of the maximum traversal distance, a closed area is defined at least at that position. However, the closed area can extend within the inside channel walls of the outwardly convex longitudinal channels until they stop at their ends (before they intersect).

In one preferred embodiment, the closed area is defined at least at the position where the traversal distance between the inside channel walls of the outwardly convex longitudinal channels reaches 20% (or less than 5% or about 0% if desired) of the maximum traversal distance. Thus, it should be noted that the "closed area" does not require an area that is physically "closed" by the outwardly convex longitudinal channels. The closed area has a maximum length (ML) and a maximum width (MW). The maximum length is defined as the longitudinal distance between the outermost walls at the both ends of the outwardly convex longitudinal channels. The maximum width is defined as the maximum traversal distance between the inside channel walls of the outwardly convex longitudinal channels. (These maximum length and width ML and MW of the closed area are shown in FIG. 6.)

In the embodiment shown in FIG. 6, the central closed area 72 is defined at least at the position P where the traversal distance TD between the outwardly convex longitudinal central channels 62 reaches 60% of the maximum traversal distance. However, the closed area 72 extends within the inside channel walls of the outwardly convex longitudinal channels 62 until they stop at their ends.

The closed area preferably has a periphery wherein 70-100% in length of the periphery is surrounded by the outwardly convex longitudinal channels. In other words, the rest (i.e., 0-30% in length) of the periphery may be surrounded by other channel(s). Preferably, 80-98% in length of the periphery of the closed area is defined by the outwardly convex longitudinal channels.

The closed area generally tries to maintain the body fluids absorbed underneath the closed area (e.g., an absorbent core). In addition, the closed area also works to prevent the material of the absorbent core from moving when it becomes wet by the absorbed body fluids.

The central closed area 72 shown in FIG. 6 has a periphery 70 defined by the inside channel walls of the two central channels 62. Preferably, 70-100% in length of the periphery 70 is surrounded by the outwardly convex longitudinal channels 62. In the embodiment shown in FIG. 6, since there is about 2% in length of the periphery 70 of the closed area having no channel portion 63, about 98% in length of the periphery 70 of the closed area 72 is defined by the outwardly convex longitudinal channels 62.

The pair of outwardly convex longitudinal central channels 62 can take any shape that defines a central closed area 72. Preferably, the central channels 62 takes an oval like shape. Preferred oval like shapes include, for example, an actual oval shape defined by mathematics and an eye shape (i.e., a shape formed by two arc like lines), and the like. In the preferred embodiment shown in FIG. 1, the central channels 62 has an eye shape consisting of two arc like lines, each of which is formed by five (5) circular arcs which are connected in series. Such oval like shapes have a maximum length ML and a maximum width MW. The central closed area 72 shown in FIG. 6 has a maximum length ML and a maximum width MW.

Preferably, the central closed area 72 has a maximum length ML of 80-220 mm and a maximum width MW of 25-70 mm. More preferably, the central closed area 72 has a maximum length ML of 130-190 mm and a maximum width MW of 35-55 mm. In the preferred embodiment shown in FIG. 1, the central closed area 72 has a maximum length ML of 160 mm and a maximum width MW of 46 mm.

Referring again to FIG. 1, the sanitary napkin 20 preferably has a rear channel 64 defining a rear closed area 74 in the rear end region 30. The rear closed area 74 can be formed not only within the rear end region 30 but both or either the central region 32 and/or the rear end region 30. For example, in the embodiment shown in FIG. 1, the rear closed area 74 is formed within the rear end region 30.

Preferably, the maximum width of the rear closed area 74 is no greater than that of the maximum width of the central closed area 72. By limiting the width of the rear closed area 74 within the maximum width of the central closed area 72, the discharged body fluids are led along the longitudinal direction more than the traversal direction by the fluids control function of the rear channels 64. Therefore, this configuration is useful to prevent the body fluids leakage from the longitudinal edges 22 of the sanitary napkin 20 in the rear end region 30. In preferred embodiment shown in FIG. 1, the maximum width of the rear closed area 74 is about same as that of the maximum width of the central closed area 72.

The rear channel 64 can take any shape that forms a closed area. The rear channel 64 preferably takes an oval like shape or an elongated U-character shape. Preferred oval like shapes include, for example, an actual oval shape defined by mathematics and an elongated U-character shape. A preferred elongated U-character shape has the traversal distance between the two arms of the elongated U-character shape decreases towards the central closed area 72 as shown in FIG. 1.

In a preferred embodiment, the sanitary napkin 20 further has an additional (or secondary) rear channel 65 within the rear closed area 74 in the rear end region 30 as shown in FIG. 1. The additional rear channel 65 does not need to form a closed area. The additional rear channel 65 is used to control the rigidity of the sanitary napkin 20 at the rear end region 30. In addition, the additional rear channel 65 also can work to maintain the absorbed body fluids in the inside area of the channel 65. The additional rear channel 65 can take any shape but it preferably takes an elongated U-character shape as shown in FIG. 1.

Referring again to FIG. 1, the sanitary napkin 20 preferably has a front channel 66 forming a front closed area 76 in the front end region 28.

The front closed area 76 can be formed not only within the front end region 28 but both the central region 32 and the front end region 28. For example, in the embodiment shown in FIG. 1, the front closed area 76 is formed within the front end region 28.

Preferably, the maximum width of the front closed area 76 is no greater than that of the maximum width of the central closed area 72. By limiting the width of the front closed area 76 within the maximum width of the central closed area 72, the discharged body fluids are led along the longitudinal direction more than the traversal direction by the fluids control function of the front channels 66. Therefore, this configuration is also useful to prevent the body fluids leakage from the longitudinal edges 22 of the sanitary napkin 20 in the front end region 28. In preferred embodiment shown in FIG. 1, the maximum width of the front closed area 76 is about same as that of the maximum width of the central closed area 72.

The front channel 66 can also take any shape that forms a closed area. The front channel 66 preferably takes a horseshoe like shape, an oval or circle like shape or a U-character shape. One example of preferred horseshoe like shape is shown in FIG. 1.

In one embodiment, the absorbent core 42 is non-profiled within the central closed area 72 so that the central region 32 has the same caliper as the outside of the central closed area 72. Preferably, the absorbent core 42 is profiled within the central closed area 72 so that the central region 32 has a caliper that is greater than the caliper of the outside of the central closed area 72 (i.e., a non-profiled portion) as shown in FIGS. 2 and 3. Herein, "profiled" means that one specified portion of a material has a caliper that is greater than that of the other portion to be compared. Herein, calipers are measured under a pressure of 0.5 psi using a circular comparator foot with a 1 inch diameter area. Typically, a profiled portion is formed by increasing the amount of material(s) at the profiled portion of the absorbent core than the other adjacent portion such that the profiled portion shows an expanded shape (or appearance) on the body surface 20A compared to the other portion. In the embodiment of FIG. 1, the absorbent core 42 contains an increased amount of material(s) within the central closed area 72 than the outside of the central closed area 72 such that the sanitary napkin 20 is profiled at the central closed area 72 as shown in FIG. 2.

Preferably, the front end region 28 and the rear end region 30 have the same or similar caliper, while the central region 32 comprises the greatest caliper portion of the sanitary napkin 20 as a result of the profiled structure. The caliper ratio of the profiled portion to the non-profiled portion preferably ranges from about 1.1:1 to about 3:1, and more preferably from about 2:1 to about 2.6:1. In the sanitary napkin 20 shown in FIG. 1, the caliper ratio of the profiled portion to the non-profiled portion is about 2.2:1.

The sanitary napkin 20 can be of any caliper, including relatively thick, relatively thin, or even very thin. The embodiment of the sanitary napkin 20 shown in FIG. 1 is intended to be an example of a relatively thick, overnight, extra protection sanitary napkin having a caliper of about 5 mm in the end regions 28 and 30 and a caliper of about 14 mm in the central region 32. It should be understood, however, when viewing these figures the number of layers of material shown may cause the sanitary napkin 20 to appear much thicker than it actually is, particularly in cross-section.

As shown in FIG. 1, the sanitary napkin 20 is asymmetrically shaped so that the rear end region 30 is larger than the front end region 28. In the preferred embodiment shown in FIG. 1, the sanitary napkin 20 is asymmetrically shaped such that the rear end region 30 has both a larger width and a longer length than the front end region 28. The widths of the front and rear end regions are defined by the traversal distance between the longitudinal edges 22 of the sanitary napkin 20. The ratio of the widths of the rear end region 30 to the front end region 28 preferably ranges from between about 1:1 and about 2.5:1. More preferably, the ratio of the widths of the rear end region 30 to the front end region 28 is about 1.4:1. The ratio of the longitudinal lengths of the front end region 28 to the central region 32 is from about 1:1 to about 1:4, and the ratio of the longitudinal lengths of the central region 32 to the rear end region 30 is from about 1:0.5 to about 1: 3. In the preferred embodiment shown in FIG. 1, the ratio of the longitudinal lengths of the front end region 28 to the central region 32 and the rear end region 30 is about 1:1.7: 2.5.

The topsheet 38 and the backsheet 40 typically have length and width dimensions generally larger than those of the absorbent core 42. The topsheet 38 and backsheet 40 extend beyond the edges of the absorbent core 42, and are joined together to form a pair of central side flaps 52 and a pair of rear side flaps 54. These topsheet 38 and backsheet 40 can be joined any means (e.g., an adhesive) known in the art.

The central side flaps 52 can be in any suitable configuration and shape known in the art. Suitable flaps are described in U.S. Pat. No. 5,389,094 issued to Lavash, et al. on Feb. 14, 1995; and U.S. Pat. No. 5,558,663 issued to Weinberger, et al. on Sep. 24, 1996.

In the embodiment shown in FIG. 1, the central side flaps 52 and the rear side flaps 54 are integral with the main body portion 25 of the sanitary napkin 20 (i.e., these flaps comprise integral extensions of the topsheet 38 and the backsheet 40 from the main body portion 25). Alternatively, these flaps can be formed by separate materials from the topsheet 38 and the backsheet 40, which are joined to the main body portion 25 of the sanitary napkin 20 in any suitable manner. In that event, the flaps are each joined to (or associated with) the main body portion 25 along a juncture, typically a longitudinally-oriented (or "longitudinal") juncture (not shown in Figs.).

The central side flaps 52 and the rear side flaps 54 are used to attach the sanitary napkin 20 to the wearer's panties or undergarment through adhesive fasteners as known in the art.

The fasteners comprise a plurality of patches of adhesive adhered to the garment surface 20B of the backsheet 40 of the sanitary napkin 20.

Figure 7:
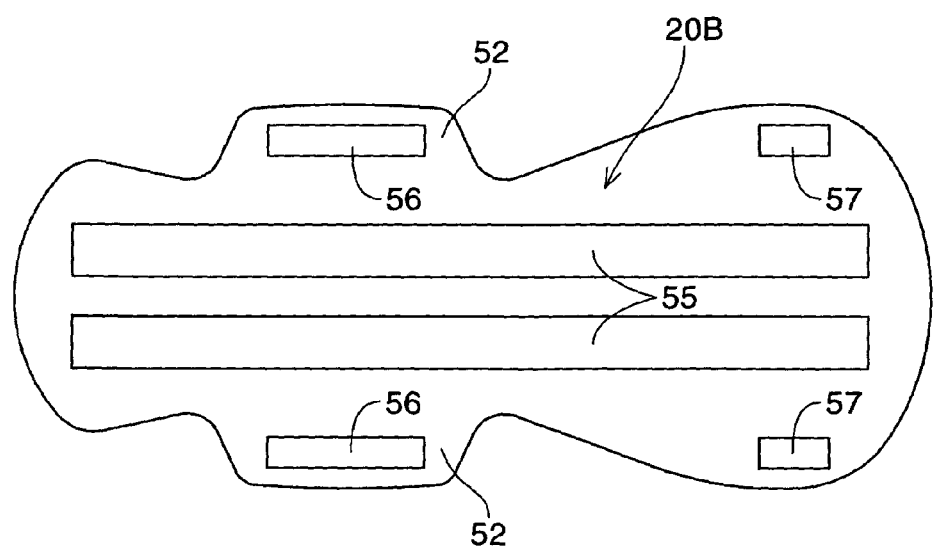
FIG. 7 is a bottom plane view of the absorbent article shown in FIG. 1.

FIG. 7 is a bottom plane view of the sanitary napkin 20 shown in FIG. 1. Typically one or two (or more if desired) adhesive patches (i.e., panty fastening adhesive 55) are disposed on the main body portion 25 of the sanitary napkin 20 such that the sanitary napkin 20 can adhere to the crotch area of the wearer's undergarment to keep the sanitary napkin 20 in place.

The panty fastening adhesive 55 is preferably at least about 50% as long as the absorbent core 42, but is preferably no greater than about 100% of the length of the core 42. The preferred length of the panty fastening adhesive 55 is between about 75% and about 90% the length of the absorbent core 42. The width of the panty fastening adhesive 55 is preferably at least about 25% of the width of the portion of the absorbent core 42 lying in the front end region 28, but should be no wider than about 100% the width of the portion of the core 42 in the front end region 28. The preferred width of the panty fastening adhesive 55 is between about 70% and about 88% of the width of the first end region core width.

In addition, a pair of additional adhesive patches (i.e., central flap adhesives 56) are disposed on the garment surface 20B of the central side flaps 52 of the sanitary napkin 20 to adhere to the undersides of the wearer's undergarment during use and to keep the napkin 20 in place to improve fit.

Preferably, another pair of additional adhesive patches (i.e., rear flap adhesives 57) are disposed on the garment surfaces 20B of the rear side flaps 54 of the sanitary napkin 20 to additionally help keep the sanitary napkin 20 in place. The rear flap adhesives 57 adheres to the undersides of the wearer's undergarment during use and to keep the napkin 20 in place to improve fit. The rear flap adhesives 57 jointly work with the continuous support layer 44 in the rear side flaps 54 to prevent the rear side flaps 54 from undesirable bunching during the use of the sanitary napkin 20.

The central side flaps 52, which have panty fasteners thereon, adhere to the underside of the wearer's undergarment. The central side flaps 52 serve to keep the sanitary napkin 20 in place during wear. Keeping the sanitary napkin 20 in place prevents skewing of the napkin 20 in the panty, and undesirable bunching. The central side flaps 52 may also assist the central region 32 in forming into the desired W-shaped configuration, and the rear end region 30 in forming the desired inverted V-shaped configuration.

These adhesive patches are preferably covered by release strips before use as known in the art. Preferably, the central side flaps 52 are folded over the topsheet 38 and they are bridged by a single (or unitary) release strip through the central flap adhesives 56. Similarly, the rear side flaps 54 are also folded over the topsheet and they are also bridged by a single (or unitary) release strip through the rear flap adhesives 57. In a particularly preferred embodiment, both the central side flaps 52 and the rear side flaps 54 are bridged by a single (or unitary) release strip. Herein, "unitary" means the release strip member can be formed by either a single material or two (or more) joined materials.

The panty fastening adhesive 55 is also covered by a release strip. If desired, the panty fastening adhesive 55 is covered by a releasable wrapper that also serves as an individual wrapper package for the sanitary napkin 20. A preferred structure is described in U.S. Pat. No. 6,074,376 issued to Mills on Jun. 13, 2000.

The sanitary napkin 20 is worn by the wearer so that the rear end region 30 is placed to the rear of the wearer's body to provide the best gluteal fit. The outwardly convex longitudinal central channels 62 assist the central region 32 of the sanitary napkin 20 in assuming a W-shaped cross-sectional configuration when the napkin 20 is laterally compressed by the wearer's thighs, thereby allowing improved contact with the wearer's genital area. This W-shaped configuration is formed by the sides compressing upwards and inwards and the center buckling upward into a convex upward configuration, with the densified region provided by the channels forming the fold lines.

In addition, due to the profiled configuration in the central region 32, the central closed area 72 is brought more closely to the source area of body fluids thereby contributing to a further better fit to the wearer's body. The profiled configuration of the central closed area 72 cooperates with the W-shaped cross-sectional configuration thereby allowing the central closed area 72 to closely fit to the wearer's genital area. This cooperative function enables an improved leakage protection at the central region 32.

The W-shape configuration of the central region 32 is transformed into an inverted V-shape configuration in the rear end region 30. The inverted V-shape configuration retains the profiled central portion of the W-shape configuration to improve gluteal fit. The rear end region 30 is thus also able to closely fit into the crevice between the wearer's buttocks (that is, in the gluteal groove) for improved protection from end soiling. This occurs while the rear end region 30 maintains its area coverage due to the size of the same and the panty fastening adhesive.

As a result, in the embodiment shown in FIG. 1, all the asymmetrical shape of the sanitary napkin 20, the embossed channels 62, 64 and 66, the central and rear side flaps 52 and 54, and the profiled configuration in the central closed area 72 cooperatively work together thereby providing an improved fit and leakage protection.

FIG. 8 is a top plane view of another preferred embodiment of the absorbent article of the present invention. In this embodiment, the absorbent article is also a relatively thick, overnight, extra protection, disposable sanitary napkin 21. It should be noted that except the channels arrangements the sanitary napkin 21 is similar to the sanitary napkin 20 which is discussed hereinabove. Referring to FIG. 8, the sanitary napkin 21 has a pair of longitudinal channels 90 formed in the front end region 28, the central region 32 and the rear end region 30; and a pair of central side flaps 52 each extending laterally outward from the central region 32. Each of the longitudinal channel 90 includes (or divided into) an outwardly convex central channel 92, an outwardly convex rear channel 94 and an outwardly convex front channel 96. The longitudinal channel 90 has (1) an outwardly convex channel portion 97 in the central region, (2) a front inwardly concave channel portion 98 at the transition area between the front end region 28 and the central region 32, and (3) a rear inwardly concave channel portion 99 at the transition area between the rear end region 30 and the central region 32.

Herein, "inwardly concave" means the longitudinal channels have a curved line shape (including a polygonal lines shape and a curved line shape) which is inwardly curved when looking from the longitudinal centerline L. The longitudinal channels 90 shown in FIG. 8 have a circular arc shape which is inwardly concave at the portions 98 and 99 when looking from the longitudinal centerline L of the sanitary napkin 20.

In one embodiment, the absorbent core 42 can be non-profiled within the central closed area 72. However, similarly to the sanitary napkin 20 shown in FIG. 1, the absorbent core 42 of the sanitary napkin 21 is preferably profiled in the central area 93 between the front inwardly concave channel portion 98 and the rear inwardly concave channel portion 99 so that the central region 32 has a caliper that is greater than the caliper of the outside of the central area 93 (i.e., a non-profiled portion).

Due to the profiled configuration in the central region 32, the central area 93 is brought more closely to the source area of body fluids thereby contributing to a further better fit to the wearer's body. The profiled configuration of the central area 93 cooperates with the W-shaped cross-sectional configuration formed by the outwardly convex central channels 92 thereby allowing the central area 93 to closely fit to the wearer's genital area. This cooperative function enables an improved leakage protection at the central region 32.

Test Methods (1) Bending Stiffness Value Measurement

The bending stiffness value is a measure of the force required to bend a specimen, which is preferably measured by a Pure Bending Tester. In this measurement, the specimen has 6.0 cm in length and 6.0 cm in width. The both side edges of the specimen is fixed between two jaws of the tester. The effective dimension for the measurement (i.e., the effective specimen sizes between the two jaws) is 4.0 cm in length and 6.0 cm in width (rectangular).

Bending force is applied to the specimen by the tester to cause a bending deformation between the curvature $K=-2.5$ $cm^{-1}$ and $2.5$ $cm^{-1}$. The specimen is bent in the direction Db with the bending axis Ba as shown in FIG. 9. The bending rate is $0.1$ $cm^{-1}$/sec. As a result, a bending hysteresis curve is obtained by the measurement as shown in FIG. 10. The horizontal axis shows the curvature K ($cm^{-1}$) and the vertical axis shows the moment M ($gf \cdot cm^2/cm$). The bending stiffness value is obtained as Bf which is the slope value of the first forward cycle of the curve at $K=0.1$ $cm^{-1}$. This measurement is carried out for 5 specimens which are cut out from one material to be measured, and the average value of the 5 specimens is defined as a "bending stiffness value" ($gf \cdot cm^2/cm$). A preferred Pure Bending Tester is available from Kato Tech Co., Ltd., Kyoto, Japan, under Code No. KES-FB2.

(2) Shear Rigidity Value Measurement

The shear rigidity value is a measure of the force required to shear a specimen, which is preferably measured by a Fabric Shear Tester. In this measurement, the specimen has 6.0 cm in length and 6.0 cm in width. The both side edges of the specimen is fixed between two jaws of the tester. The effective dimension for the measurement (i.e., the effective specimen sizes between the two jaws) is 6.0 cm in length and 5.0 cm in width (rectangular).

Figure 11:
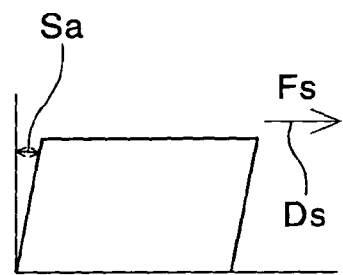
FIG. 11 is a schematic diagram of a specimen explaining the measurement for the shear rigidity.
Figure 12:
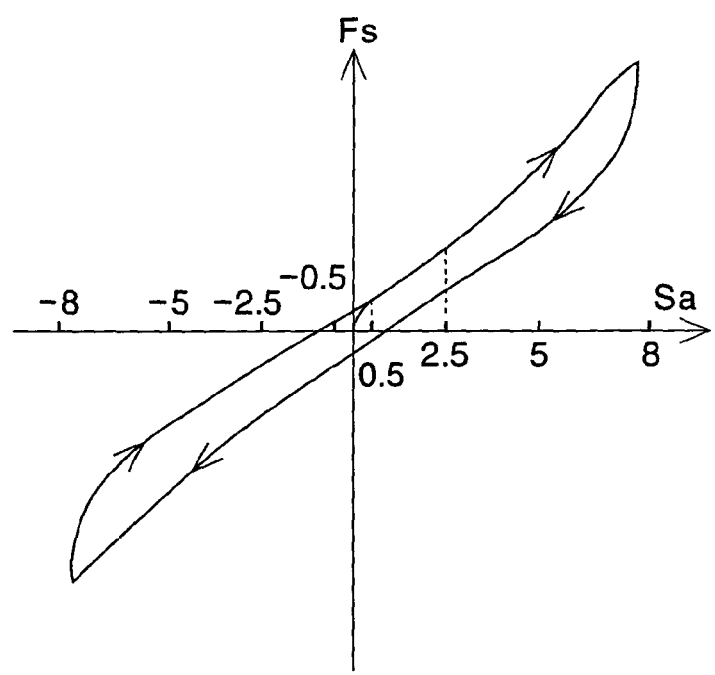
FIG. 12 is a graph showing a shear hysteresis curve of a specimen.

Shear force Fs is applied to the specimen by the tester to cause a shear deformation between the shear angle $Sa=0$ degree and 8 degrees. The specimen is sheared in the direction Ds as shown in FIG. 11 (Note: the direction Ds corresponds to the length direction of the specimen). The shearing rate is 0.417 mm/sec. As a result, a shearing hysteresis curve is obtained by the measurement as shown in FIG. 12. The horizontal axis shows the shear angle Sa (degrees) and the vertical axis shows the shear force Fs (gf·cm). The shear rigidity value is obtained as G which is the average slope value of the shearing hysteresis curve between the shear angle $Sa=0.5$ and 2.5 degrees. This measurement is carried out for 5 specimens which are cut out from one material to be measured, and the average value of the 5 specimens is defined as a "shear rigidity value" (gf/cm·degree). A preferred Fabric Shear Tester is available from Kato Tech Co., Ltd., Kyoto, Japan, under Code No. KES-FB1.

EXAMPLES

Example 1

An air laid nonwoven web which is available from Kang Na Hsiung Enterprise Co., Ltd., Taipei, Taiwan, under Code No. AL080-BL01-10 is prepared. This nonwoven web has basis weight of 80 g/m², density of 0.07 g/cm³, and thickness of 1.16 mm. This nonwoven web is formed by a mixture of chemical pulp (or cellulose) fibers and polyethylene/polypropylene bi-component fibers through an air through process. This nonwoven web is a continuous material which has a bending stiffness value of 0.79 gf·cm²/cm and a shear rigidity value of 5.85 gf/cm·degree.

Example 2

An air laid nonwoven web which is available from BBA (China) Airlaid Co., Ltd., Tianjin, China, under Code No. B667M077P25 is prepared. This nonwoven web has basis weight of 77 g/m², density of 0.096 g/cm³, and thickness of 0.80 mm. This nonwoven web is formed by two layers which are joined by multi-bonding process (i.e., a combination bonding of heart and latex), which include a polypropylene nonwoven (Layer 1); and a mixture of chemical pulp (or cellulose) fibers, polyethylene/polyester bi-component fibers (Layer 2). This nonwoven web is a continuous material which has a bending stiffness value of 2.74 gf·cm²/cm and a shear rigidity value of 5.32 gf/cm·degree.

Example 3

An air laid nonwoven web which is available from BBA (China) Airlaid Co., Ltd., Tianjin, China, under Code No. B889M18017 is prepared. This nonwoven web has basis weight of 180 g/m², density of 0.144 g/cm³, and thickness of 1.25 mm. This nonwoven web is formed by a mixture of chemical pulp (or cellulose) fibers, polyethylene/polyester bi-component fibers, ethylene vinyl acetate latex binder and super absorbent polymers (acrylic acid and sodium acrylate copolymer) through a multi-bonding process (combination of thermal bonding and latex bonding). This nonwoven web is a continuous material which has a bending stiffness value of 6.33 gf cm²/cm and a shear rigidity value of 8.15 gf/cm·degree.

Example 4

An air laid nonwoven Web which is available from Kang Na Hsiung Enterprise Co., Ltd., Taipei, Taiwan, under Code No. AL070-CS10$^{-10}$ is prepared. This nonwoven web has basis weight of 70 g/m², density of 0.07 g/cm³, and thickness of 1.00 mm. This nonwoven web is formed by a mixture of chemical pulp (or cellulose) fibers and polyethylene/polypropylene bi-component fibers through an air through process. This nonwoven web is a continuous material which has a bending stiffness value of 4.35 gf cm²/cm and a shear rigidity value of 3.17 gf/cm·degree.

All documents cited in the Detailed Description of the Invention are, are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a pair of longitudinal edges, front and rear transverse edges, a front end region, a rear end region, and a central region disposed between the front and rear end regions, wherein the front end region has a width defined between the longitudinal edges, the rear end region has a width defined between the longitudinal edges, and the ratio of the width of the rear end region to the width of the front end region ranges between 1:1 and 2.5:1, the absorbent article comprising:
a liquid pervious topsheet;
a liquid impervious backsheet;
an absorbent core disposed between the topsheet and the backsheet at least in the central region and the rear end region, the absorbent core having a pair of longitudinal edges;
a pair of central side flaps each extending laterally outward from the corresponding longitudinal edge of the absorbent core in the central region;
a pair of rear side flaps each extending laterally from the corresponding longitudinal edge of the absorbent core in the rear end region;
a continuous support layer disposed on the backsheet in the rear end region, the continuous support layer extending across the rear end region from one of the pair of rear side flaps to the other of the pair of rear side flaps, including laterally into the pair of rear side flaps;
a pair of outwardly convex longitudinal central channels formed at least in the central region, the traversal distance between the pair of outwardly convex longitudinal central channels decreasing towards both ends of the channels to define a central closed area having a maximum width, wherein the traversal distance between a pair of outwardly convex longitudinal central channels reaches 20% of the maximum width;
a rear channel defining a rear closed area in the rear end region, the rear channel being discontinuous from the pair of outwardly convex longitudinal central channels; and
a secondary channel within the rear closed area;
wherein the continuous support layer is absent in the central side flaps; and
wherein the continuous support layer includes a continuous material which has a shear rigidity value of between 3.0 gf/cm·degree and 10.0 gf/cm·degree in the longitudinal direction.

2. The absorbent article of claim 1 wherein each of the rear side flaps has a continuous material which has a bending stiffness value of 0.4-10.0 gf·cm²/cm in the longitudinal direction.

3. The absorbent article of claim 1 wherein the traversal distance between the pair of outwardly convex longitudinal central channels reaches 5% of the maximum width.

4. An absorbent article having a pair of longitudinal edges, front and rear transverse edges, a front end region, a rear end region, and a central region disposed between the front and rear end regions, wherein the front end region has a width defined between the longitudinal edges, the rear end region has a width defined between the longitudinal edges, and the ratio of the width of the rear end region to the width of the front end region ranges between 1:1 and 2.5:1, the absorbent article comprising:
a liquid pervious topsheet;
a liquid impervious backsheet;
an absorbent core disposed between the topsheet and the backsheet at least in the central region and the rear end region, the absorbent core having a pair of longitudinal edges;
a pair of central side flaps each extending laterally outward from the corresponding longitudinal edge of the absorbent core in the central region;
a pair of rear side flaps each extending laterally from the corresponding longitudinal edge of the absorbent core in the rear end region;
a continuous support layer disposed on the backsheet in the rear end region, wherein the continuous support layer extends across the rear end region from one of the pair of rear side flaps to the other of the pair of rear side flaps, including laterally into the pair of rear side flaps, and wherein the continuous support layer is absent in the central side flaps;
a pair of outwardly convex longitudinal central channels formed at least in the central region, the traversal distance between the pair of outwardly convex longitudinal central channels decreasing towards both ends of the channels to define a central closed area having a maximum width, wherein the traversal distance between the pair of outwardly convex longitudinal central channels reaches 20% of the maximum width;
a rear channel defining a rear closed area in the rear end region, the rear channel being discontinuous from the pair of outwardly convex longitudinal central channels;
a secondary channel within the rear closed area; and
a uniform adhesive layer disposed between the continuous support layer and the backsheet in the rear end region;
wherein the uniform adhesive layer uniformly bonds the continuous support layer to the backsheet in the rear end region.

5. The absorbent article of claim 1 or 4 wherein the continuous support layer is disposed between the topsheet and the backsheet in the rear end region.

6. The absorbent article of claim 1 or 4 wherein the continuous support layer is disposed between the absorbent core and the backsheet in the rear end region.

7. The absorbent article of claim 1 or 4 wherein the continuous support layer includes a nonwoven material having a basis weight of 40-200 g/m².

8. The absorbent article of claim 7 wherein the nonwoven material includes an air-laid nonwoven material.

9. The absorbent article of claim 4 wherein the uniform adhesive layer has a basis weight of about 1.0-13 g/m².

10. The absorbent article of claim 4 wherein the uniform adhesive layer is formed by a hot-melt adhesive.

* * * * *